United States Patent [19]

Venugopalan et al.

[11] Patent Number: 5,225,427
[45] Date of Patent: Jul. 6, 1993

[54] 10-SUBSTITUTED ETHER DERIVATIVES OF DIHYDROARTEMISININ, PROCESS FOR THEIR PREPARATION AND THEIR USE AS ANTIPROTOZOAL AGENTS

[75] Inventors: Bindumadhavan Venugopalan, Thane, Maharashtra, India; Chintamani P. Bapat, Urbana, Ill.; Pravin J. Karnik, Thane, India; Bansi Lal; Dipak K. Chatterjee, both of Bombay, India; Subramani N. Iyer, Bombay, India; Richard H. Rupp, Konigstein/Taunus, Fed. Rep. of Germany

[73] Assignee: Hoechst Aktiengesellschaft, Frankfurt am Main, Fed. Rep. of Germany

[21] Appl. No.: 799,179

[22] Filed: Nov. 27, 1991

Related U.S. Application Data

[63] Continuation-in-part of Ser. No. 416,256, Oct. 2, 1989, abandoned.

[30] Foreign Application Priority Data

Oct. 4, 1988 [EP] European Pat. Off. ........ 88116378.6

[51] Int. Cl.$^5$ .................. A61K 31/335; C07D 493/18
[52] U.S. Cl. ................... 514/378; 514/232.8; 514/253; 514/321; 514/422; 514/414; 514/450; 544/148; 544/378; 546/197; 548/247; 548/454; 548/526; 549/348
[58] Field of Search ............. 549/348; 514/450, 232.8, 514/253, 321, 422, 414, 378; 548/247, 454, 526; 544/148, 378; 546/197

[56] References Cited

U.S. PATENT DOCUMENTS

| | | | |
|---|---|---|---|
| 4,791,135 | 12/1988 | Lin et al. | 514/450 |
| 5,011,951 | 12/1988 | Buchs et al. | 549/348 |
| 5,019,590 | 5/1991 | Avery et al. | 549/348 |
| 5,023,353 | 6/1991 | McChesney et al. | 549/348 |
| 5,057,501 | 10/1991 | Thornfeldt | 514/450 |

FOREIGN PATENT DOCUMENTS

362730  4/1990  European Pat. Off. .

OTHER PUBLICATIONS

Gu et al, Chemical Abstracts, vol. 94, No. 24954 (1981).
Li et al, Chemical Abstracts, vol. 97, No. 92245 (1982).
Venugopalan et al, Chemical Abstracts, vol. 115, No. 126988 (1991) (Abstract for EP362730).
Lin, et al., Chemical Abstracts, vol. 107, No. 168241 (1987).
Yu, et al., Chemical Abstracts, vol. 105, No. 24454 (1986).
Wu, et al., Chemical Abstracts, vol. 97, No. 16656 (1982).
Hanson, et al., "Phenylpiperazine-Based Radiopharmaceuticals for Brain Imaging. 3. Synthesis and Evaluation of Radioiodinated 1-Alkyl-4-phenylpiperazines," J. Med. Chem., vol. 30, pp. 29-34 (1987).
Brossi, et al., "Arteether, a New Antimalarial Drug: Synthesis and Antimalarial Properties," J. Med. Chem., vol. 31, pp. 645-650 (1988).
Luo, et al., "The Chemistry, Pharmacology, and Clinical Applications of Quinghaosu (Artemisinin) and Its Derivatives," Medicinal Research Reviews, vol. 7, No. 1, pp. 29-52 (1987).
Yu, et al., "Synthesis of Artemisinin Analogs Containing Halogen, Nitrogen or Sulfer Atoms," Chemical Abstracts, Abstract No. 95:150917e, vol. 95, No. 17 (1981).

Primary Examiner—Emily Bernhardt
Attorney, Agent, or Firm—Finnegan, Henderson, Farabow, Garrett & Dunner

[57] ABSTRACT

10-substituted ether derivatives of 3α, 12α-Epoxy-3,4,5 5aα, 6,7,8,8aα,9,10,12β, 12a-dodecahydro-10-hydroxy-3β,6α,9β-trimethylpyano-(4,3-j) (1,2) benzodioxepin, also known as Dihydroartemisinin or Dihydroquinghaosu (DHQ), pharmaceutically acceptable salts thereof, processes for their preparation and their use as chemotherapeutics against protozoal infections are provided.

7 Claims, No Drawings

10-SUBSTITUTED ETHER DERIVATIVES OF DIHYDROARTEMISININ, PROCESS FOR THEIR PREPARATION AND THEIR USE AS ANTIPROTOZOAL AGENTS

This application is a continuation-in-part application of U.S. patent application Ser. No. 07/416,256, filed Oct. 2, 1989, now abandoned.

This invention relates to 10-substituted ether derivatives of 3α, 12α-Epoxy-3,4,5,5aα,6,7,8,8a-dodecahydro-10-hydroxy-3β,6α,9-62 -trimethylpyano-(4,3-j) (1,2) benzodioxepin, also known as Dihydroartemisinin or Dihydroquinghaosu (DHQ) and pharmaceutically acceptable salts thereof, processes for their preparation and their use as chemotherapeutics against protozoal infections.

Artemisinin and its ethers are reviewed in *Medicinal Research Reviews*, Vol. 7, No. 1, 29–52 (1987) and *J. of Medicinal Chemistry*, 31, 645 (1988).

Although compounds of the prior art have been reported to possess antimalarial activity, they have invariably had to be administered parenterally for activity to be demonstrated at sufficiently low doses. Recrudescence was also observed at a rate of 10–30% in a month after administration with such parenteral forms. The use of these compounds is thus claimed as useful only for cerebral malaria. Surprisingly, it has now been determined that the novel derivatives of artemisinin described herein are characterized by two special qualities:

(a) they possess potent antimalarial activity when administered orally to animals, becoming thus potential agents for all forms of malaria resulting from susceptible and resistant form of pathogenic Plasmodium strains and (b) they possess antiprotozoal activity in general and in particular antiamoebic activity against the protozoa Eimera tenella, hitherto not known for artemisinin or any of its known derivatives.

Thus, the instant invention is directed to 10-substituted ether derivatives of dihydroquinghaosu as represented by the general formula I:

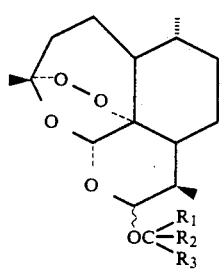

wherein, $R_1$ is hydrogen or a lower alkyl, $R_2$ is hydrogen, a lower alkyl or an alkoxy alkyl, and $R_3$ is an acyl, alkoxy alkyl, alkynyl, heterocycle or heterocyclic alkyl, and pharmaceutically acceptable salts thereof.

In the formulae presented herein, the various substituents are illustrated as joined to a pyrano(4,3-j)(1,2)benzodioxepin nucleus by one of two notations a solid line (—) indicating a substituent which is in the β-orientation (i.e. above the plane of the molecule), and a broken line (- - -) indicating a substituent which is in the α-orientation (i.e. below the plane of the molecule). The formula have all been drawn to show the compounds in their absolute configuration. In as much as the starting materials having a pyrano(4,3-j)(1,2)benzodioxepin nucleus are naturally occurring or are derived from naturally occurring materials, they as well as the final products, have a pyrano (4,3-j) (1,2)benzodioxepin nucleus in the single absolute configuration depicted herein. The processes of the present invention, however, are intended to apply as well to the synthesis of pyrano)4,3-j) (1,2)benzodioxepines of the racemic series.

In addition to the optical centers of a pyrano(4,3-j) (1,2)benzodioxepin nucleus, the substituents thereon may also contain chiral centers contributing the optical properties of the compounds of the present invention and providing a means for the resolution thereof by conventional methods, for example, by the use of optically active acids. A wavy line (~) indicates that the substituents can either be in the α-orientation or β-orientation. The present invention comprehends all optical isomers and racemic forms of the compounds of the present invention where such compounds have chiral centers in addition to those of the pyrano (4,3-j) (1,2)benzodioxepin nucleus.

The term alkyl stands for $C_1$-$C_8$ straight or branched chain carbon compounds such as methyl, ethyl, propyl, butyl, isopropyl, and t-butyl. The term alkynyl stands for straight or branched chain carbon compounds containing one or more triple bonds, and may in addition contain a double bond. Examples of alkynyl groups are 3-methyl-1-pentoynyl, 1-butynyl, 3-methyl-1-butynyl, 2-butynyl-1-hydroxymethyl.

The term heterocycle stands for piperazino, morpholino, piperidino, pyyrolidino, phthalimido, isoxazolyl, optionally substituted at one or more places by alkyl, alkoxy, hydroxy, halogen, or aryl groups optionally substituted by a carboxyl group.

Preferred compounds of the invention are listed in Table 1, and their biological activity in Table 2.

TABLE 1

| No. | $R_1$ | $R_2$ | $R_3$ | | m.p. °C. | solvent for crystallisation | Yield (%) |
|---|---|---|---|---|---|---|---|
| 1. | H | CH₃ | COCH₃ | (β) | OIL | — | 33 |
| 2. | H | CH₂OCH(CH₃)₂ | CH₂OCH(CH₃)₂ | (α) | OIL | — | 39 |
| 3. | H | CH₃ | C≡CH | (β) | 91–93 | Pet. ether | 35 |
| 4. | CH₃ | CH₃ | C≡CH | (β) | 58–60 | Pet. ether | 57 |
| 5. | CH₃ | C₂H₅ | C≡CH | (β) | OIL | Pet. ether | 62 |
| 6. | H | H | CH₂–N(phthalimido-Cl) | (β) | 150–152 | Chloroform/ Diisopropyl ether | 32 |
| 7. | H | H | isoxazole-C₆H₄-COOH | (α + β) | 150–152 | Methylene chloride/ Pet. ether | 55 |
| 8. | H | H | chloro-isoxazole | (β) | 106 | — | 53 |
| 9. | H | H | bromo-isoxazole | (β) | OIL | — | 63 |

Particularly preferred compounds of the invention are:

3α,12-60 -Epoxy-3,4,5,5aα,6,7,8aα,9,10,12β,12a-dodecahydro-10-β[1-acetylethoxy]-3β,6α,9β-trimethylpyrano(4,3-j) (1,2)benzodioxepin.

3α,12α-Epoxy-3,4,5,5aα,6,7,8,8aα,9,10,12β12a-dodecahydro-10α-[1,3-bis(isopropyoxy) propyl-2]oxy-3β,6α9β-trimethylpyrano (4,3-j)(1,2)benzodioxepin.

3α,12α-Epoxy-3,4,5,5aα6,7,8,8a,9,10,12β,12a-dodecahydro-10β-(3-butynyl-2-oxy)-3 -butynyl-2-oxy)-3β6α,9β-trimethylpyrano(4,3-j) (1,2)benzodioxepin.

3α,12α-Epoxy-3,4,5,5aα,6,7,8,8aα,9,10,12β,12a-dodecahydro-10β-(2-methyl-3-butynyl-2-oxy)-3β,6α,9β-trimethylpyrano (4,3-j)(1,2)benzodioxepin.

3α,12α-Epoxy-3,4,5,5aα,6,7,8,8aα,9,10,12β1-2adodecahydro-10β-(2-ethyl-3-butynyl-2-oxy)-3β,6α,9β-trimethylpyrano (4,3-j)1,2)benzodioxepin.

3α,12α-Epoxy-3,4,5,5aα,6,7,8,8aα,9,10,12β,12a-dodecahydro-10β-[2-(4-chlorophthalimido)-ethoxy]-3β,6α9β-trimethylpyrano (4,3-j)1,2)benzodioxepin.

5-[3α,12α-Epoxy-3,4,5,5aα,6,7,8,8aα,9,10,12β,12a-dodecahydro-3β6α,9β-trimethylpyrano (4,3-j)(1,2)benzodioxepin-10-oxy] methyl-3-(4-carboxyphenyl)isoxazole.

5-[3α,12α-Epoxy-3,4,5,5aα,6,7,8,8aα,9,10,12β,12a-dodecahydro-3β,6α9β-trimethylpyrano(4,3-j)1,2)benzodioxepin-10-β-yl]oxymethyl-3-chloroisoxazole.

5-[3α,12α-Epoxy-3,4,5,5aα,6,7,8,8aα,9,10,12β,12a-dodecahydro-3β,6α,962 -trimethylpyrano (4,3-j)(1,2)benzodioxepin-10β-yl]oxymethyl-3bromoisoxazole.

The process for the preparation of compounds of the invention comprises treating compounds of the formula II with compounds of the formula III, wherein X and R have the same meaning as defined above, preferably in the presence of BF₃-etherate at a temperature of 0° -10° C. under stirring for half an our to six hours.

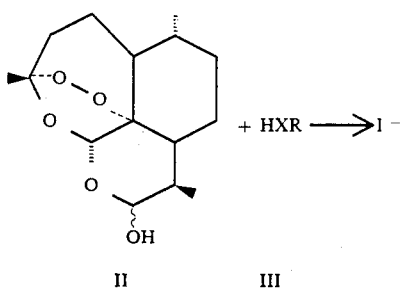

II        III

The reaction is preferably carried out in organic solvents such as benzene and chloroform. For completion of the reaction, the reaction mixture may be heated to the boiling point of the solvent used. The compounds of the invention are isolated by diluting the reaction mixture with water, separating the organic layer, washing it with water, concentrating the organic layer and purifying it by flash column chromatography using a silica gel column. Compounds of the formula II are obtained by the procedure reported in the literature (Acta. Chim. Sinica. 37, 129 (1979)).

The compounds of formula I may be administered in different manners, preferably perorally or parenterally, in doses ranging from 2.5 to 100 mg/kg of body weight. As antimalarial drugs, dosage unit forms such as dragees or capsules for oral administration or solutions and suspensions respectively for injections, each containing 100 to 400 mg of active substance, are preferred. Such dosage units are administered once to three times daily depending upon the condition of the patient.

For oral administration, there may be used in particular tablets, dragees, capsules, powders or granules which contain the active substance together with the usual carriers, adjuvants and/or excipients such as starch, cellulose powder, talcum, magnesium stearate, sugar, gelatin, calcium, carbonate, finely divided silicic acid, carboxymethyl cellulose or similar substances.

For parenteral administration, in particular for intramuscular injections, there may be used sterile suspensions, for example, oily suspensions prepared with the use of sesame oil, vegetable oil, castor oil or synthetic triglycerides, optionally with the simultaneous use of surface active substances such as sorbitan fatty acid esters. Furthermore, there may also be used aqueous suspensions prepared, for example, with the use of ethoxylated sorbitan fatty acid esters, optionally with the addition of thickeners such as polyethylene glycol or carboxymethyl cellulose.

BIOLOGICAL EVALUATION METHODOLOGY

The evaluation of blood-schizontocidal activity "28-day test" described by Rather and Fink [W. H. O. Report on the Scientific Working Group on the Chemotherapy in Malaria, TDR/Chemal 3-rd Review, 85.3, Geneva, Jun. 3-5, 1985 and references contained therein] was followed.

Mice: All experiments were carried out in random bred male and female Swiss mice obtained from the Hoechst India Limited breeding house at Mulund, Bombay. The animals were free from Eperythrozoon coccoides. The animals received food pellets and water ad lib and were kept at 22-25° C. room temperature.

Parasite: Plasmodium berghei K-173 strain drug-sensitive and P. berghei (NS) moderately resistant to chloroquine were obtained from London School of Hygiene and Tropical Medicines. The strains produce lethal infection at $1 \times 10^7$ parasitized red blood cells per mouse when inoculated intraperitoneally.

Administration of compounds: The compounds were administered orally or subcutaneously as per methods described by Rather and Fink [W. H. O. Report on the Scientific Working Group on the Chemotherapy in Malaria, TDR/Chemical 3rd Review, 85.3, Geneva, Jun. 3-5, 1985 and references contained therein].

compounds of the invention were homogenized in double refined Kardi oil or peanut oil or corn oil with one or two drops of polyoxyethylenesorbitan monooleate ((R)Tween-80, Sigma Chanicallo, England) and such suspensions were used for subcutaneous inoculation in mice. The drugs were administered for 5 days. 1st dosing was done within 2 hours of infection (D+0), followed by D+1, D+2, D+3 and D+4.

Observation of the treated mice: The blood smears were prepared at different intervals from D+4 and continued up to D+28. Blood smears were drawn from the terminal end of the trail and stained in Giemsa. Mice which were free from P. berghei on D+28 were considered as completely cured.

Results obtained with compounds of Formula I of the invention are listed in Table 2.

TABLE 2

Antimalarial Activity

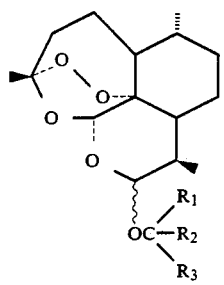

| | | | | | ACTIVITY | |
|---|---|---|---|---|---|---|
| | | | | ROUTE OF ADMINISTRATION × | No. of animals cured/ treated | No. of animals cured/ treated |
| $R_1$ | $R_2$ | $R_3$ | DOSE mg/kg | 5 | D + 7 | D + 28 |
| 1. H | $CH_3$ | $COCH_3$ | (β) 5.0 | s.c. | 6/6 | 6/6 |

TABLE 2-continued

Antimalarial Activity

| | R₁ | R₂ | R₃ | | DOSE mg/kg | ROUTE OF ADMINIS- TRATION × 5 | ACTIVITY | |
|---|---|---|---|---|---|---|---|---|
| | | | | | | | No. of animals cured/ treated D + 7 | No. of animals cured/ treated D + 28 |
| 2. | H | CH₂OCH(CH₃)₂ | CH₂OCH(CH₃)₂ | (α) | 5.0 | s.c. | 6/6 | 4/6 |
| 3. | H | CH₃ | C≡CH | (β) | 5.0 | s.c. | 6/6 | 6/6 |
| 4. | CH₃ | CH₃ | C≡CH | (β) | 5.0 | s.c. | 6/6 | 6/6 |
| 5. | CH₃ | C₂H₅ | C≡CH | (β) | 5.0 | s.c. | 6/6 | 4/6 |
| | | | | (β) | 10.0 | s.c. | 6/6 | 4/6 |
| 6. | H | H | [CH₂-N-phthalimide-Cl] | (β) | 10.0 | s.c. | 6/6 | 4/6 |
| 7. | H | H | [isoxazole-C₆H₄-COOH] | (α + β) | 50.0 | s.c. | 8/8 | 8/8 |
| 8. | H | H | [isoxazole-Cl] | (β) | 5.0 | s.c. | 5/5 | 5/5 |
| 9. | H | H | [isoxazole-Br] | (β) | 5.0 | s.c. | 6/6 | 5/6 |
| Artemisinin | | | | | 100.0 | p.o. | 4/10 | 0/10 |
| | | | | | 50.0 | p.o. | 0/6 | 0/6 |
| | | | | | 20.0 | s.c. | 4/6 | 0/6 |
| | | | | | 10.0 | s.c. | 0/6 | 0/6 |

ANTIAMOEBIC EVALUATION METHODOLOGY

In vitro tests were carried out in Jones medium using a polyaxenic culture, the strain of Entamoeba histolytica was BY 80 isolated in Bombay in Hoechst Pharmaceuticals in 1980. The inoculum used was $3 \times 10^4$ amoebae per tube. The derivatives under test were dissolved in DMSO and serial dilution tests were carried out in the same medium. Microscopical examination was made after 48 hours of incubation at 37° C. The minimum inhibitory concentration (MIC) was determined by observing the the amoebae under microscope for physical damage (lysis or immobility) of the trophozoites. Controls with and without 0.2% DSMO were run to compare the growth of amoebae with the treated group. Meronidazole was used as a standard drug.

As a typical representative example, Compound Nos. 5 and 7 in Table 1 when tested as described above showed antiamoebic activity at a MIC concentration of 200 ug/ml.

The following examples illustrate the invention but do not limit the scope of the invention.

EXAMPLE 1

3α,12α-Epoxy-3,4,5,5aα,6,7,8,8aα,9,10,12β,12a-dodecahydro-10β-(1-acetylethoxy) -3β,6α,9β-trimethylpyrano)4,3-j) (1-2)benodioxepin To a solution of dihydroquinghaosu (0.10 g, 0.0004 m) and 3-hydroxy-2-butanone (0.2 g, 0.002 m) in 15 ml chloroform was added BF₃ etherate (3 drops) at 0° C., and after the addition, the mixture was slowly brought to room temperature and stirred for 6 h. The reaction mixture was then diluted with water and the organic layer was separated, washed thoroughly with water, dried over anhydrous sodium sulphate and concentrated to obtain the residue, as an oil which was purified by flash column chromatography over silica gel using petroleum ether: ethyl acetate (8.7:1.3) as eluants. Concentration of the first few fractions gave the pure 3α,1-2α-Epoxy-3,4,5,5aα,6,7,8,8aα,9,10,12β12a-dodecahydro-10β-(1-acetylethoxy)-3β, 6α, 9β-trimethylpyrano[4,3-j] [1,2]benzodioxepin as an oil in 33% yield.

EXAMPLE 2

3α,12β,Epoxy-3,4,5,5aα,6,7,8,8aα,9,10,12β,12a-doecahydro-10α-[1,2-bis(isopropoxy) -propyl-2]oxy-3β,6α,9β-trimethylpyrano[4,3j][1,2]benzodioxepin.

To a solution of dihydroquinghaosu (0.05 g 0.002 m) and 1,3-bis(isopropoxy)propan-2-ol (0.05 g, 0.0003 m) in 15 ml chloroform was added BF$_3$ etherate (2 drops at 0° C., and after the addition, the mixture was stirred in an ice bath for an additional 15 minutes. The reaction mixture was then diluted with water, dried over anhydrous sodium sulphate and concentrated to obtain the residue, as an oil which was purified by flash column chromatigraphy over silica gel using petroleum ether: ethyl acetate (8.5:1.5) as eluants to give 3α,12α-Epoxy-3,4,5,5aα, 6,7,8,8aα,9,10α,12β,12a-dodecahydro-10α-[1,3-bis(isopropoxy)-propyl-2]oxy-3β6α, 9β-trimethyl pyrano [4,3-j][1,2]benzodoxepin as an oil in 39% yield.

Following the procedure described in the above example, the compounds reported in Table 1 were prepared similarly using an appropriate nucleophile in place of 1,3-bis(isopropoxy)propan-2-ol.

EXAMPLE 3

5-[(3α,12α-Epoxy-3,4,5,5aα,6,7,8,8aα,9.10,12β,12a-dodecahydro-3β,6α, 9β-trimethylpyrano(4,3-j)(1,2)-benzodioxepin)-10-oxymethyl]-3-(4-carboxyl phenyl) isoxazole.

The solution of 5-[(3α,12α-Epoxy-3,4,5,5aα,6,7,8-,8aα,9, 10,12β,12a-dodecahydro-3β,6α,9β-trimethylpyrano[4,3-j][1, 2]benzodioxepin)-10-oxymethyl]-3-[4-carboethoxyphenyl]isoxazole (1.150 g, 1.0003 m) in 16 ml 2.5% methanolic potassium hydroxide was allowed to stand for a day. The reaction mixture was concentrated, and the residue was dissolved in water. The aqueous solution was then acidified with acetic acid, and the separated solid was filtered to obtain 5-[3α,12α-epoxy-3,4,5aα,6,7,8, 8aα,9,10,12β,12a-dodecahydro-3β,6α,9β-trimethylpyrano[4,3-j][1,2]benzodioxepin)-10-oxymethyl]-3-(4-carboxyphenyl)isoxazole which was recrystallized from methylene chloride/petroleum ether, m.p 150–152° C. in 55% yield.

We claim:

1. A 10-substituted ether derivative of dihydroquinghaosu having the formula I:

wherein
R$_1$ is hydrogen;
R$_2$ is hydrogen; and
R$_3$ is a —CH$_2$-phthalimido group of isoxazoyl group, which may be substituted by one or more halogen atoms or phenyl groups which are optionally substituted by a carboxyl group;
or pharmaceutically acceptable salts thereof.

2. A 10-substituted ether derivative according to claim 1, having the formula:
3α12α-Epoxy-3,4,5,5aα,6,7,8,8aα,9,10,12β,12a-dodecahydro-10β-[2-(4-chlorophthalido)-ethoxy]-3β,6α,9β-trimethylpyrano (4,3-j) (1,2) benzodioxepin.

3. A 10-substituted ether derivative according to claim 1, having the formula:
5-[3α,12α-Epoxy-3,4,5,5aα,6,7,8,8aα,9,10,12β,12a-dodecahydro-3β,6α,9β-trimethylpyrano (4,3-j)(1,2)benzodioxepin-10-oxy] methyl-3-(4-carboxyphenyl)isoxazole.

4. A 10-substituted ether derivative according to claim 1, having the formula:
5-[3α,12α-Epoxy-3,4,5,5aα,6,7,8,8aα,9,10,12β,12a-dodecahydro-3β,6α, 9β-trimethylpyrano(4,3-j) (1,2) benzodioxepin-10-βyl]oxymethyl-3-chloroisoxazole.

5. A 10-substituted ether derivative according to claim 1, having the formula:
5-[3α,12α-Epoxy-3,4,5,5aα,6,7,8,8aα,9,10,12β,12a-dodecahydro-3β,6α, 9β-trimethylpyrano(4,3-j) (1,2) benzodioxepin-10β-yl)]oxymethyl-3-bromoisoxazole.

6. A pharmaceutical composition for the treatment and prophylaxis of diseases which are caused by infections with protozoa, comprising an effective amount of a compound according to claim 1 in combination with pharmaceutically acceptable carriers, adjuvants or excepients.

7. A method of treating diseases caused by infections with protozoa, comprising administering an effective amount of a compound according to claim 1 to a host in need of such treatment.

* * * * *

UNITED STATES PATENT AND TRADEMARK OFFICE
CERTIFICATE OF CORRECTION

PATENT NO. : 5,225,427
DATED : July 06, 1993
INVENTOR(S) : Bindumadhavan Venugopalan et al.

It is certified that error appears in the above-indentified patent and that said Letters Patent is hereby corrected as shown below:

Claim 2, column 10, line 26, insert a comma after "3a".

Claim 4, column 10, line 40, change "10-Byl" to --10-B-yl--.

Signed and Sealed this

Twenty-ninth Day of March, 1994

Attest:

BRUCE LEHMAN

Attesting Officer

Commissioner of Patents and Trademarks